United States Patent [19]

Holderness

[11] Patent Number: 5,180,526

[45] Date of Patent: Jan. 19, 1993

[54] CLEANING OF SOLUTIONS OF ALKYLPHOSPHATES

[75] Inventor: Stewart G. Holderness, Cheshire, United Kingdom

[73] Assignee: British Nuclear Fuels, plc, Warriington, England

[21] Appl. No.: 788,793

[22] Filed: Sep. 30, 1991

[30] Foreign Application Priority Data

Sep. 29, 1990 [GB] United Kingdom ............... 9021264

[51] Int. Cl.⁵ ............................................. G21F 9/08
[52] U.S. Cl. ................................. 252/631; 252/626; 252/364; 252/DIG. 17; 210/638; 423/7
[58] Field of Search ....... 252/626, 631, 364, DIG. 17; 423/10, 7; 210/638

[56] References Cited

U.S. PATENT DOCUMENTS

| | | | |
|---|---|---|---|
| 2,809,091 | 10/1957 | Jonke | 423/10 |
| 2,885,260 | 5/1959 | Maraman et al. | 223/8 |
| 3,112,275 | 11/1963 | Pollock et al. | 252/631 |
| 3,708,508 | 1/1973 | Schulz | 252/364 |
| 3,959,435 | 5/1976 | Mills et al. | 423/10 |
| 4,358,426 | 11/1982 | Tallent et al. | 423/10 |
| 4,394,269 | 7/1983 | Tallent et al. | 210/690 |
| 4,544,530 | 10/1985 | Tsai et al. | 423/10 |
| 4,741,857 | 5/1988 | Horwitz et al. | 252/184 |
| 4,950,425 | 8/1990 | Rowbottom et al. | 252/631 |
| 5,082,602 | 1/1992 | Uetake et al. | 252/627 |

FOREIGN PATENT DOCUMENTS

| | | |
|---|---|---|
| 2216719 | 3/1981 | Fed. Rep. of Germany . |
| 62-239099 | 10/1987 | Japan . |
| 1360945 | 7/1974 | United Kingdom . |

*Primary Examiner*—Donald P. Walsh
*Assistant Examiner*—Ngoclan T. Mai
*Attorney, Agent, or Firm*—Larson and Taylor

[57] ABSTRACT

A process for cleaning solutions of an alkylphosphate in a hydrophobic organic solvent. The process involves the steps of washing the solution with aqueous sulphuric acid, and contacting the washed solution with an ion exchange material. The ion exchange material may be a resin of the type designated as styrene divinyl benzene copolymers.

23 Claims, No Drawings

CLEANING OF SOLUTIONS OF ALKYLPHOSPHATES

The present invention relates to the cleaning of solutions of alkylphosphates, and in particular to alkylphosphates dissolved in a hydrophobic organic solvent. Such solutions are used in solvent extraction processes involved in the production of uranium from uranium ore.

During use, especially in the recovery of waste uranium from the main ore conversion process, both the alkylphosphates and the solvent gradually become increasingly degraded as a result of chemical changes due to radiolysis and attack by acids. In time the degradation products interfere with the solvent extraction process to such a degree that the solution has to be replaced and the discarded uranium-contaminated material disposed of at considerable cost.

It has now been found that by first removing, by means of a suitable reagent, sufficient complexed nitric acid (and other complexed species of uranium and iron) from the impure alkylphosphate solution, and subsequently subjecting the said solution to an ion-exchange treatment, a solution can be produced which satisfies the requirements for re-usability.

According to the present invention, there is provided a process for cleaning a degraded solution of an alkyl phosphate in a hydrophobic organic solvent the solution being degraded in the solvent extraction of uranium ore and containing complexed nitric acid and complexed species comprising uranium therein, the process comprising the steps of washing the said solution with aqueous sulphuric acid to remove the complexed nitric acid and the complexed species and contacting the washed solution with an ion exchange material.

The invention is particularly directed at the treatment of solutions of trialkylphosphate in which the alkyl groups range from ethyl to octyl, especially butyl, and in particular n-butyl. The hydrophobic organic solvent for the trialkylphosphate is normally a hydrocarbon liquid, usually a mixture of hydrocarbons, for example obtained from the distillation of petroleum, 10 typically a kerosene boiling between 180° C and 290° C, of which odourless kerosene is frequently employed.

The concentration of alkylphosphate in the hydrophobic organic solvent can vary widely and compositions can be treated in which the alkylphosphate is concentrated or very dilute. In general the alkyl phosphate will be present in the solution at a concentration of about 5 to 50% on a volume to volume basis. Typically, a solution for treatment after use in the production of nuclear grade uranium would comprise about 20–40% v/v of tributylphosphate (TBP) in odourless kerosene.

Decommissioned alkylphosphate solutions in hydrocarbon liquid, that is, solutions which have become degraded in use to such an extent that they can no longer be used, can contain significant amounts of uranium and nitric acid mainly in an organically complexed form.

The concentration of aqueous sulphuric acid used for washing the alkylphosphate solution can vary widely and generally falls within the range 30% v/v to 0.1% v/v $H_2SO_4$ preferably 5% v/v to 0.1% v/v H A typical concentration used is about 4% v/v $H_2SO_4$ in water.

The washing method may be any method suitable for efficient contact between the organic phase and the aqueous phase and which provides a contact time sufficient for efficient mass transfer. A counter-current flow system is preferred and appropriate means such as box mixer-settlers or pulsed columns may be employed to effect contact.

The ratio of the volume of alkylphosphate solution to the volume of aqueous sulphuric acid during washing can vary widely, and is usually between 20 and 0.05 volumes of aqueous sulphuric acid to one volume of alkylphosphate solution.

In general, a temperature of ambient or above during washing is favoured, and temperatures in the range 15° C. to 60° C., preferably 18° C. to 25° C., are suitable.

The first step of the process of the invention, namely washing with aqueous sulphuric acid, is primarily of importance in the removal of organically complexed nitric acid and/or free nitric acid from the alkylphosphate solution. Removal of such contaminants facilitates the subsequent ion-exchange step in the process of the invention by preventing, it is believed, the adsorption of nitrate ions on to the ion exchange material which would lead to a disastrous loss of the ability of the ion exchange material to remove degradation products from the alkylphosphate solution.

The washing step is also beneficial in removing uranium, wholly or partially, from the alkylphosphate solution. Apart from avoiding a reduction in ion-exchange capacity, the ion-exchange material is not contaminated by radioactive material, thereby facilitating safe disposal of the material used to regenerate the ion exchange resin.

The ion-exchange materials used in the second step of the process according to the invention are preferably chosen from anionic ion exchange materials, inorganic or organic, for example resins of the chemical type or types designated as styrene divinyl benzene copolymers. Weakly basic anionic resins are preferred. Mixed anionic/cationic resins are also useful, for example Duolite MB5113, available from Diamond Shamrock (Polymers) Ltd. The ion exchange resin may also advantageously be of the macroreticular type.

Examples of preferred ion-exchange resins for use in the process of the invention include the strongly basic anionic resin designated Amberlyst A26 and particularly the weakly basic anionic resin Amberlyst A21, both available from the Rohm & Haas Co. Amberlyst A21 is a macroreticular resin having an amino functional group and an average pore diameter of 900–1300 Angstroms whereas Amberlyst A26, also a macroreticular resin, has a quaternary ammonium functional group and a pore-diameter of 400–700 Angstroms.

An ion-exchange resin of some interest is the anionic Duolite A116 available from Diamond Shamrock (Polymers) Ltd).

In use, the ion-exchange resins are normally in the hydroxyl ionic forms.

The ion-exchange step of the process of the invention can be carried out by any convenient method known in the art. Contact between the washed solution and the ion-exchange resin is preferably carried out in a packed column of the ion exchange resin.

The operation of the ion-exchange column is preferably carried out on a continuous basis until regeneration of the resin becomes necessary.

It is desirable to filter the washed solution before it enters the column so as to avoid fouling of the resin with any solid particles present which could reduce its efficiency and effective life.

It is important to ensure that sufficient contact time between the washed solution and the ion-exchange resin is provided in order to ensure an adequate degree of purification of the alkylphosphate solution being treated. In general, the longer the contact time the more efficient is the ion-exchange process. It is convenient to express contact time in a packed column in terms of the number of "bed-volumes" passed through the column per hour, usually abbreviated to Bv/hr. By way of example contact times of between 0.1 Bv/hr and 20 Bv/hr can be used, but a contact time of 0.1–1.0 Bv/hr is preferred.

The progress of cleaning the solution of alkyl phosphate can conveniently be followed throughout the process of the invention by measuring the Retained Uranium (RU) value of the solution expressed as micrograms of uranium per milliliter ($\mu$g U/ml) of solution. This value is most readily determined by an empirical method in which a sample of the solution is saturated with uranium by the addition of uranyl nitrate, extracted five times with dilute (0.06% w/v) nitric acid and the amount of uranium remaining measured by a standard technique.

Although not essential, it may be useful in certain cases to wash the alkylphosphate solution with a weak alkali, for example aqueous sodium carbonate, before it is subjected to the first step of washing with aqueous sulphuric acid in the process of the invention.

After use, the ion exchange resin may be regenerated by any suitable method known in the art. We prefer to use aqueous sodium hydroxide as regenerant, usually at a concentration of 4% to 10% W/V. The amount of regenerant is usually between 100% and 500% of the theoretical capacity of the ion exchange column.

The invention is illustrated by, but not limited to, the following Examples.

EXAMPLE 1

Six hundred liters of solvent (comprising 120 liters of Tributyl Phosphate (TBP) and 480 liters of odourless kerosene) were taken from the Recovery Line solvent extraction plant in the production of nuclear grade uranium and washed with 4% aqueous sulphuric acid until free from uranium. The solvent and aqueous streams were fed counter-currently through a series of box mixer-settlers, at a solvent to aqueous ratio of 2:1 to effect washing.

The solvent was then passed at 1.5 liters an hour (0.5 Bv/hr) through an ion-exchange column containing 3 liters of Amberlyst A21.

The RU value (as hereinbefore described) of the solvent was reduced from 189 $\mu$gU/ml to 11 $\mu$gU/ml by passing the solvent once through the ion-exchange resin.

EXAMPLE 2

900 ml of solvent (comprising 180 ml of TBP and 720 ml of odourless kerosene) from the Recovery Line solvent extraction plant was washed repeatedly with 2% sulphuric acid in a series of box mixer-settlers as in Example 1, until free from uranium.

The solvent was then passed at 1.5 ml/hr (0.1 Bv/hr) through an ion-exchange column containing 15 ml of Amberlyst A26.

The RU values of the solvent before and after the ion-exchange treatment were 82 $\mu$gU/ml and 25 $\mu$gU/ml respectively.

EXAMPLE 3

One liter of solvent (comprising 200 ml of TBP and 800 ml of odourless kerosene) from the Recovery Line solvent extraction plant was washed repeatedly with 10% sulphuric acid in a series of box mixer-settlers as in Example 1, until free from uranium.

The solvent was then passed at 150 ml/hr (1.0 Bv/hr) through an ion-exchange column containing 150 ml of Duolite A116, in the hydroxide form.

The RU values of the solvent before and after the ion-exchange treatment were 275 $\mu$gU/ml and 6 $\mu$gU/ml respectively.

I claim:

1. A process for cleaning a degraded solution of an alkylphosphate in a hydrophobic organic solvent, the solution being degraded in the solvent extraction of uranium from uranium ore and containing complexed nitric acid and complexed species comprising uranium therein, the process comprising the steps of washing the solution with aqueous sulphuric acid, and contacting the washed solution with an ion exchange material.

2. A process as claimed in claim 1, wherein the solution comprises trialkylphosphate.

3. A process as claimed in claim 2, wherein the alkyl is selected from alkyl groups ranging from ethyl to octyl.

4. A process as claimed in claim 3, wherein the alkyl group comprises butyl.

5. A process as claimed in claim 4, wherein the alkyl group comprises n-butyl.

6. A process as claimed in claim 1, wherein the alkylphosphate in the solution has a concentration of between about 5% and 50% by volume.

7. A process as claimed in claim 6, wherein the alkylphosphate in the solution comprises tributylphosphate at a concentration between about 20% and 40% by volume.

8. A process as claimed in claim 1, wherein the has a concentration aqueous sulphuric acid is between about 30% and 0.1% by volume.

9. A process as claimed in claim 8, wherein the aqueous sulphuric acid concentration is between 10% and 0.1% by volume.

10. A process as claimed in claim 9, wherein the aqueous sulphuric acid concentration is between 10% and 2% by volume.

11. A process as claimed in claim 1, wherein the aqueous sulphuric acid is present in an amount between 20 and 0.05 volumes of said aqueous sulphuric acid to one volume of said alkylphosphate solution.

12. A process as claimed in claim 1, wherein the washing step carried out at a temperature between 15° C. and 60° C.

13. A process as claimed in claim 12, wherein the temperature is between 18° C. and 25° C.

14. A process as claimed in claim 1, wherein the ion exchange material comprises an anionic ion exchange material.

15. A process as claimed in claim 14, wherein the anionic ion exchange material comprises resin comprising a styrene divinyl benzene copolymer.

16. A process as claimed in claim 15, wherein the resin is weakly basic.

17. A process as claimed in claim 15, wherein the resin comprises a mixture comprising anionic and cationic resins.

18. A process as claimed in claim 15, wherein the resin comprises macroreticular resin.

19. A process as claimed in claim 1, wherein said solution and the aqueous sulphuric acid are in countercurrent flow relationship.

20. A process as claimed in claim 1, wherein the ion exchange material is packed in a column, and the is contacted with washed solution and the ion exchange material at a rate between 0.1 and 20 bed-volumes per hour.

21. A process as claimed in claim 20, wherein said contact rate is between 0.1 and 1.0 bed-volumes per hour.

22. A process as claimed in claim 1, including the step of washing the alkylphosphate solution with a weak alkali before the alkylphosphate solution is washed with the aqueous sulphuric acid solution.

23. A process for cleaning a degraded tributylphosphate solution in a hydrophobic organic solvent, the solution being degraded in the solvent extraction of uranium from uranium ore and containing complexed nitric acid and complexed species comprising uranium therein, the process comprising, a) washing the tributylphosphate counter-currently, initially with a weak solution comprising sodium carbonate, and then with aqueous sulfuric acid at a solvent to aqueous ratio of about 2:1 to remove the complexed nitric aid and the complexed species, the concentration of the sulfuric acid being about 4% by volume, and the temperature during washing being between 18° C. and 25° C.

b) filtering the washed solution, and c) contacting the filtered tributylphosphate solution with a macroreticular anionic styrene divinyl benzene copolymer ion exchange material arranged in a column for a contact time of between 01.1 and 1.0 bed-volumes per hour.

* * * * *